US010175167B2

(12) United States Patent
Grinderslev et al.

(10) Patent No.: US 10,175,167 B2
(45) Date of Patent: Jan. 8, 2019

(54) OPTICAL SENSOR FOR DETECTING ACCUMULATION OF A MATERIAL

(71) Applicant: TE Connectivity Corporation, Berwyn, PA (US)

(72) Inventors: Soren Grinderslev, Hummelstown, PA (US); Igor Stouklov, Walnut, CA (US); Mark Benton, Hoffman Estates, IL (US)

(73) Assignee: TE CONNECTIVITY CORPORATION

( * ) Notice: Subject to any disclaimer, the term of this patent is extended or adjusted under 35 U.S.C. 154(b) by 0 days.

(21) Appl. No.: 15/471,852

(22) Filed: Mar. 28, 2017

(65) Prior Publication Data

US 2018/0284017 A1    Oct. 4, 2018

(51) Int. Cl.
    *G01N 21/00*     (2006.01)
    *G01N 21/41*     (2006.01)
    *G01N 21/94*     (2006.01)

(52) U.S. Cl.
CPC ......... *G01N 21/4133* (2013.01); *G01N 21/94* (2013.01); *G01N 2021/945* (2013.01); *G01N 2201/0826* (2013.01)

(58) Field of Classification Search
None
See application file for complete search history.

(56) References Cited

U.S. PATENT DOCUMENTS

| | | | | |
|---|---|---|---|---|
| 4,201,914 A | * | 5/1980 | Perren ................. | G01F 23/2927 250/341.2 |
| 4,274,705 A | * | 6/1981 | Miller ................. | G01F 23/2927 385/12 |
| 4,286,464 A | * | 9/1981 | Tauber ............... | G01F 23/2924 340/619 |
| 4,782,331 A | * | 11/1988 | Martens ............... | B64D 15/20 340/580 |
| 4,797,660 A | * | 1/1989 | Rein, Jr. ............... | G08B 19/02 244/134 F |
| 4,803,470 A | * | 2/1989 | Fineman ............... | G01N 21/43 340/583 |
| 4,808,813 A | * | 2/1989 | Champetier ........... | G01N 21/94 250/223 B |
| 4,932,747 A | * | 6/1990 | Russell ................. | G02B 6/04 219/121.6 |
| 4,998,022 A | * | 3/1991 | Tregay ................. | G01F 23/2925 250/577 |
| 5,534,708 A | * | 7/1996 | Ellinger .............. | G01F 23/2927 250/577 |

(Continued)

*Primary Examiner* — Shawn Decenzo
*Assistant Examiner* — Jarreas C Underwood (57) ABSTRACT

A sensor for detecting the level of accumulation of a material along an axis in a fluid environment, the sensor comprising (a) an optically transparent body having a third refractive index and an exposed surface defining a length extending at least partially in the direction of the axis; (b) at least one light delivery source for delivering light to the body such that the light is distributed along the length of the exposed surface; and at least one light receiver for receiving reflected light from the length of the exposed surface, wherein the amount of the reflected light depends on the level of the material accumulated along the length of the exposed surface.

28 Claims, 7 Drawing Sheets

(56) References Cited

U.S. PATENT DOCUMENTS

| | | | | |
|---|---|---|---|---|
| 5,596,320 | A * | 1/1997 | Barnes | B64D 15/20 250/574 |
| 5,880,480 | A * | 3/1999 | Ellinger | G01F 23/2925 250/577 |
| 6,010,095 | A * | 1/2000 | Hackmeister | B64D 15/20 244/134 F |
| 6,049,088 | A * | 4/2000 | Harding | G01F 23/2925 250/577 |
| 6,668,645 | B1 * | 12/2003 | Gilmour | G01F 23/2927 250/573 |
| 6,750,977 | B2 * | 6/2004 | Otsubo | C23C 16/4401 118/712 |
| 6,921,911 | B2 * | 7/2005 | Siepmann | G01F 23/2927 250/577 |
| 7,199,388 | B2 * | 4/2007 | Omatoi | G01F 23/2922 250/573 |
| 7,312,713 | B2 * | 12/2007 | Alfano | B64D 15/20 250/339.07 |
| 7,586,419 | B2 * | 9/2009 | Ikiades | B64D 15/20 324/671 |
| 75,864,191 | | 9/2009 | Ikiades et al. | |
| 7,719,697 | B2 * | 5/2010 | Roques | G01B 11/0633 340/962 |
| 7,969,566 | B2 * | 6/2011 | Smith | G01N 21/15 340/583 |
| 9,222,824 | B1 * | 12/2015 | Belden | G01F 23/2927 |

\* cited by examiner

OPTICAL SENSOR FOR DETECTING ACCUMULATION OF A MATERIAL

FIELD OF INVENTION

The present invention relates, generally, to optical sensors, and, more specifically, to the detection of material levels in a fluid environment such as, for example, the level of icing on an aircraft wing.

BACKGROUND

Aircraft icing is a dangerous condition. The formation of ice on the exposed leading edges of wing components changes the aerodynamics of the aircraft and may lead to a decrease in lift and an increase in drag. Typically, the ice formation occurs in clouds at altitudes less than 20,000 ft. (Above this level, the water molecules have already been transformed to ice and will typically just bounce off the foil.) When an aircraft flies through an ice formation zone—i.e., clouds with high moisture content below 20,000 ft. —ice will deposit on the aero-foil. It is critical that excess ice deposits are detected and removed before they cause aerodynamic and mechanical malfunctions and reduce fuel consumption.

Over the years there have been many attempts to design suitable ice detectors based on varying concepts, including, for example, monitoring the conductivity of an exposed rod and monitoring the frequency change of an exposed vibrating element. These electrical and electro mechanical approaches are subject to significant false readings and require continuous maintenance.

Of particular interest herein are optical ice detection approaches. For example, U.S. Pat. No. 6,010,095 discloses a device for sending a beam of light parallel to a surface being monitored for ice. If there is no ice accretion, the beam is reflected back to a light detector. If there is ice accumulation with a height sufficient to interfere with the emitted light beam, the ice will cause a diffraction and re-direction of the beam, thus preventing it from reflecting back to the detector. This device will determine ice accumulation only if it has reached a certain point. Another optical detector configuration is described in U.S. Pat. No. 7,586,419, which comprises an array of optical sensors, which are mounted flush with an outer surface of an aircraft skin, and a centrally located optical emitter. Light is emitted by the emitter outwardly of the aircraft surface, and the layer of accreted ice diffuses the emitted radiation scattered and reflected. The diffused radiation is detected by the sensors, and the spatial distribution of the detected intensity diffused radiation about the emitter can be used to calculate the thickness of the layer of ice and the type of ice. This device requires that the optical sensors be mounted flush with the surface being monitored, which may require drilling or otherwise modifying the aircraft surface. Obviously, any structural modification to a wing component is undesirable as it may compromise the function or structural integrity of the wing component.

Therefore, there is need for a simplified, rugged optical sensor design, which can determine both the presence and the thickness of ice on a monitored surface without modification to the monitored surface. The present invention fulfills this need among others. Indeed, the sensor of the present invention can be applied to measure the level of accumulation of any material, providing the material has a refractive index different from its environment.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention is based on an incident light beam changing direction at an interface of a sensor and the materials being measured due to the differences in the refractive indexes of the materials. In other words, the manner in which the light beam changes direction at the sensor interface is indicative of which material is contacting the sensor interface. Thus, depending on the change in the direction of the beam, the refractive index of the material at the sensor interface, and hence the material's identity, can be determined.

In one embodiment, the present invention simplifies the determination of the change in direction of the incident beam by configuring the sensor to either reflect or transmit the beam at the sensor's interface depending on what material is contacting the sensor's interface. As is known, total internal reflection (TIR) is a phenomenon, which occurs when a propagated wave strikes an interface at an angle larger than a particular "critical angle" with respect to the normal to the surface. Because the sensor is detecting the presence of materials having two different refractive indexes, in one embodiment, the incident angle can be selected such that TIR will occur for first material, but not the second. This way the amount of light reflected will be indicative of the amount of second material contacting the exposed surface, or conversely the amount of light transmitted will be indicative of the first material at the exposed surface.

Therefore, by monitoring only the TIR contribution, the measurement of reflective light (and thereby transmitted light) can be measured within the sensor itself and there is no need for measuring transmitted light outside the sensor. In other words, the material can be measured based on its effect on the boundary of the sensor, thereby avoiding the need to interact physically with the material/environment. Therefore, the sensor of the present invention is well suited for applications in harsh, dangerous and explosive environments. Furthermore, the sensor need not be integrated into the surface being monitored, but can be positioned on the surface, thereby avoiding any significant modification to the monitored surface, which is critical in aircraft applications.

Although the present invention is suited well for measuring icing on aircraft wings, it can be used in any application to measure the level of accumulation of a material in a fluid environment. The accumulation may be the material settling on a monitored surface as the result of gravity or other environmental force. As the material accumulates, its contact with the sensor progresses from one end of the interface surface to the other, displacing the fluid of the environment as it goes.

In one embodiment, the invention relates to a sensor for detecting the level of accumulation of a material along an axis in a fluid environment, the material having a first refractive index and the fluid having a second refractive index different from the first refractive index. In one embodiment the sensor comprises: (a) an optically transparent body having a third refractive index and at least one exposed surface defining a length, the exposed surface being configured to be exposed to the environment and positioned with the length extending at least partially along the axis; (b) at least one light delivery source for delivering light to the body such that the light is distributed along the length of the exposed surface; and (c) at least one light receiver for receiving reflected light from the length of the exposed surface, wherein the amount of the reflected light depends on the level of the material accumulated along the length of the exposed surface. In one embodiment, the sensor also comprises (d) a controller to determine the level of accumulation of the material along the length of the exposed surface based on at least the reflected light.

In another embodiment, the invention relates to a sensor in combination with an structure having a monitored surface, the sensor for detecting the level of accumulation of a material along an axis in a fluid environment, wherein the axis is perpendicular to the monitored surface, the material having a first refractive index and the fluid having a second refractive index different from the first refractive index. The sensor comprises: (a) an optically transparent body having a third refractive index and at least one exposed surface defining a length, the exposed surface being exposed to the environment and positioned with the length extending at least partially along the axis; (b) at least one light delivery source for delivering light to the body such that the light is distributed along the length of the exposed surface; (c) at least one light receiver for receiving reflected light from the length of the exposed surface, wherein the reflected light depends on the level of the material accumulated along the length of the exposed surface; and (d) a controller to determine the level of accumulation of the material along the length of the exposed surface based on at least the reflected light.

In another embodiment, the invention relates to a method for detecting the level of accumulation of a material along an axis in a fluid environment, the material having a first refractive index and the fluid having a second refractive index different from the first refractive index. In one embodiment the method comprises: (a) transmitting an incident beam along a length of an exposed surface of an optically transparent body having a third refractive index, the exposed surface being configured to be exposed to the environment and positioned with its length extending at least partially along the axis; (b) receiving reflected light from the length of the exposed surface, wherein the amount of the reflected light depends on the level of the material accumulated along the length of the exposed surface.

DETAILED DESCRIPTION

Figure 1:
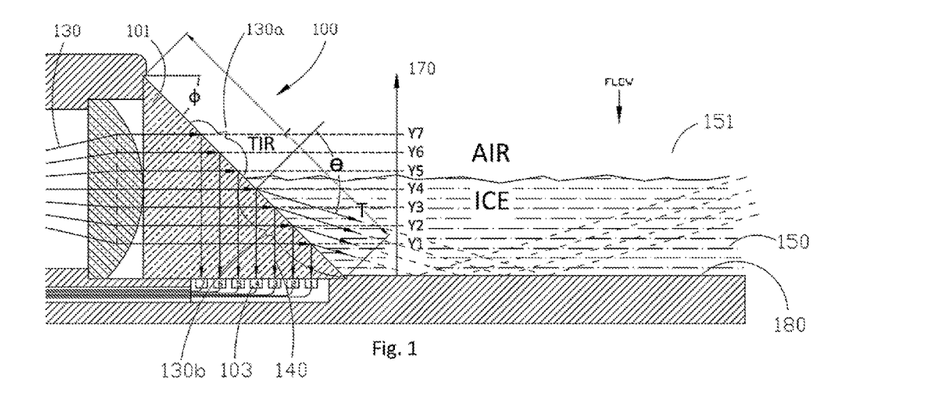
FIG. 1 shows one embodiment of the invention as used as an icing sensor.

Referring to FIG. 1, a sensor 100 of the present invention is shown. The sensor 100 is configured for detecting the level of accumulation of a material 150 along an axis 170 in a fluid environment 151. (As used herein, a fluid environment is the environment in which the material accumulates. The fluid(s) of the fluid environment may be gaseous (e.g., air) or liquid (e.g., water), and is (are) displaced by the accumulation of the material.) The material 150 has a first refractive index and the fluid has a second refractive index different from the first refractive index. The sensor comprises an optically transparent body 101 having a third refractive index and at least one exposed surface 101a defining a length l. One of the first or second refractive indexes is lower than the third refractive index. The exposed surface 101a is configured to be exposed to the environment 151 and positioned with the length l extending along the axis 170. The sensor 100 also comprises at least one light delivery source (not shown, see, e.g., FIG. 2, light delivery source 203) for delivering light 130 to the body such that the light is distributed along the length of the exposed surface. Additionally, the sensor 100 comprises at least one light receiver 103 for receiving reflected light 140 from the length of the exposed surface. The reflected light 140 depends on the level of the material accumulated along the length of the exposed surface. The sensor may also include a controller 250 (shown schematically in FIG. 2) to determine the level of accumulation of the material along the length of the exposed surface based on at least the reflected light. Each of these elements is described in greater detail below and with respect to alternative embodiments.

Figure 8A:
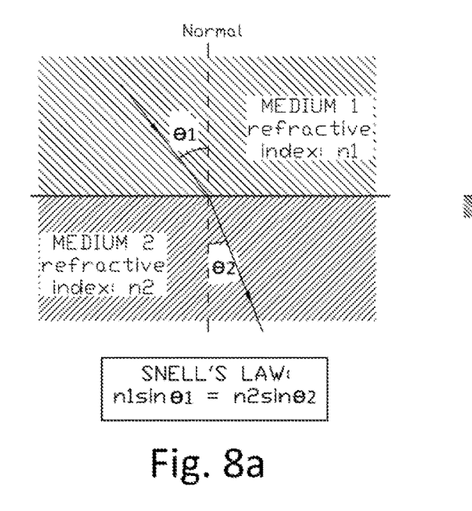
FIGS. 8a & 8b illustrate known optical properties.
Figure 8B:
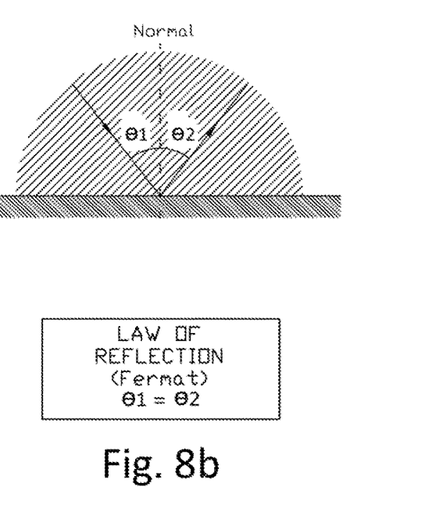

The sensor of the present invention relies on Snell's Law and/or the Law of Reflection derived from Fermat's Principle as shown in FIGS. 8a and 8b, respectfully. In FIG. 8a, 'n' indicates the refractive index of a material and θ1 is the incident angle of the beam onto the interface of the two materials. As shown in FIG. 8a, and dictated by Snell's Law, light will change direction at the interface of two materials having dissimilar refractive indexes, n1 and n2, according to n1 sin θ1=n2 sinθ2, wherein θ1 and θ2 are the incident and exiting angles respectively of light going through the first and second materials with respect to the perpendicular of the interface of the two materials. Therefore, light changes direction at the interface of two materials having different refractive indexes based on the refractive indexes. Referring to FIG. 8b, the Law of Reflection, as derived from Fermat's Principle, simply states that the angle of incidence θ1 equals the angle of reflection θ2.

The present invention is based on a light beam changing direction at the interface of two different materials. More specifically, the present invention involves transmitting light through an optically-transparent body having at least one surface exposed to two or more materials having different refractive indexes. The manner in which the light beam changes direction at the exposed surface is indicative of which material is contacting the exposed surface. In other words, if the direction of the incident beam is known, and the change in direction of the beam is measured, the refractive index of the other material at the interface can be determined. Therefore, if the materials likely to contact the exposed surface are limited and known, then they can be identified by their refractive index.

In one embodiment, the present invention simplifies the determination of the change in direction of the incident beam by configuring the exposed surface to reflect one material and to transmit the other. As is known, total internal reflection (TIR) is a phenomenon, which occurs when a propagated wave strikes an interface at an angle larger than a particular "critical angle" with respect to the normal to the surface. If the refractive index is lower on the other side of the interface and the incident angle is greater than the critical angle, the wave cannot pass through and is entirely reflected. The critical angle is the angle of incidence above, which the total internal reflection occurs, and can be calculated as follows: $\theta crit=\sin^{-1}(n2/n1)$, with $n1>n2$.

Because the sensor is detecting the presence of materials having two different refractive indexes, in one embodiment, the incident angle can be selected such that TIR will occur for first material, but not the second. This way the amount of light reflected will be indicative of the amount of second material contacting the exposed surface, or conversely the amount of light transmitted will be indicative of the first material at the exposed surface. For example, if the first material is ice (which has a refractive index of 1.33), the second material is air (which has a refractive index of 1.0), and the transparent body is glass (which has a refractive index of approximately 1.5), then the TIR or the T/R ratio is ruled mainly by the angle of incidence since both materials have a refractive index below the glass body. In such an embodiment, the angle of incidence is chosen such that it is below the critical angle for one material and above the critical angle for the other material. Returning to the example above, TIR will occur for air contacting the body at an angle of incidence of greater than 42° (the critical angle for air/glass). Likewise, transmission from the body into ice will occur at an approximate angle of incidence below 62.4° (the critical angle for ice/glass). Therefore, an angle of incidence of greater than 42° and below 62° will result in TIR for the air/body boundary and transmittance for the ice/glass boundary. In one embodiment, the angle of incidence is 45° owing to the simplicity of manufacturing a simple prism, although it should be understood that variations in the angle of exposed surface and delivered beams is permissible providing that the incident beam on the exposed surface is below critical angle for one material and below that of the other.

In another embodiment, TIR and transmittance is determined not just by the angle of incidence, but also by the selection of the body material. Specifically, the body material may have a refractive index which is below that of a first material and above that of a second material. This way, only the boundary of the body and the second material will cause TIR; TIR is not possible for the first material. For example, in one embodiment, if the first material is ice with a refractive index of 1.33 and the second material is air with the refractive index of 1, then the body may be made from a transparent material having a refractive index less than 1.33 but greater than 1 such that TIR is possible only at the air/body boundary, providing that the incident angle is also configured to be above the critical angle. For example, for n(body)=1.25, n(air)=1.0, and n(ice)=1.33, then a 45 degree incidence from body to air results in T=95% and R=5%, not TIR. To achieve the TIR, the incident angle must be greater than 53.13°, which results in T=99.7% into ice.

It should be understood that by using TIR, the measurement of reflective light (and thereby transmitted light) can be measured within the sensor itself and there is no need for measuring transmitted light outside the sensor. In other words, the material can be measured based on its effect on the boundary of the sensor, thereby avoiding the need to interact with the material.

Such a sensing approach can be used to measure the level of accumulation of a material in a fluid environment. The accumulation may be the material settling on a monitored surface. This settling or buildup may be the result of gravity, e.g. a tank being filled with fluid, or other environmental force, the apparent wind on the wing of an airplane causing ice to buildup on the wing's edge, or fluid momentum in a pipe causing scale to build up on the inside of the pipe. As the material accumulates, it moves from one end of the exposed surface to the other, displacing the fluid of the environment as it moves.

Figure 3A:
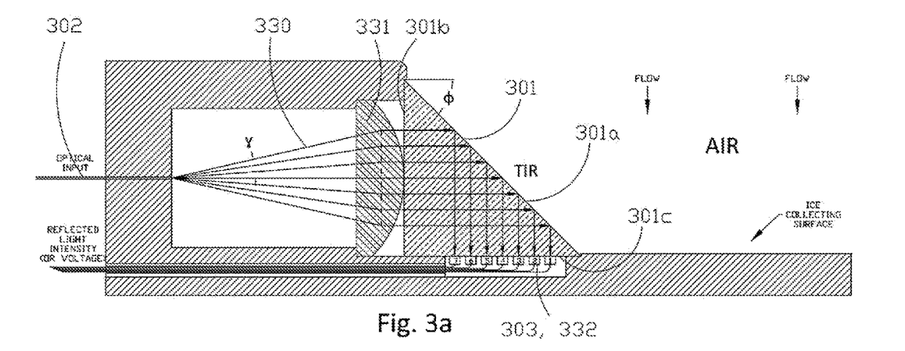
FIGS. 3a & 3b show the embodiment of FIG. 1 with a correlation between the different light beams and the level of material accumulated on the monitored surface.
Figure 3B:
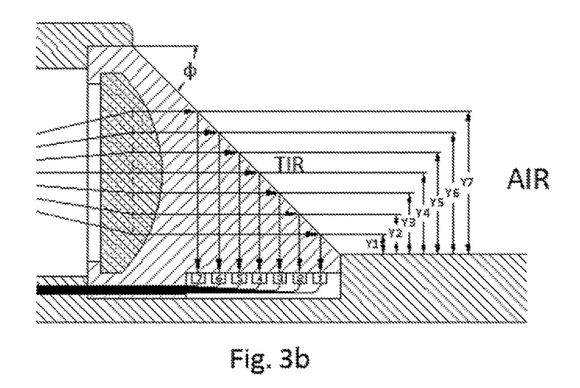

This concept is explained with respect to the present invention in connection with FIGS. 3a & 3b. A single fiber is used as a delivery source 302 for the transmission of a light beam 330 through a lens 331. The exit angle γ of the marginal ray 330 from the fiber source 302 is determined by the fiber numerical aperture (NA) and the launch condition. The lens 331 collimates the beam for further transmission. The beam is sent through a first surface 301b of the optically transparent body 301 and reaches the exposed surface 301a, which is exposed by an angle Φ relative to the beam axis. The exposed surface 301a is exposed to the environment that requires measurement. In combination with the NA of the launch fiber, the lens design is chosen to assure that a large beam expansion illuminates a substantial portion of the length of the exposed surface.

In one embodiment, the angle Φ of the exposed surface is chosen to ensure that total internal reflection (TIR) occurs when the exposed surface 103a is contacting the fluid (e.g. air) of the environment. This means that all rays incident onto the exposed surface are reflected internally 100% with an angle equal to the incident angle. For an inclination angle of Φ=45°, all optical body materials having a refractive index n>1.42 will experience TIR when the fluid environment being investigated is air/atmosphere (n=1.00).

When the fluid is air, all light within the collimated beam is being reflected down through a second surface 301c of the body 301 and to the light receiver 303, which in this embodiment, is a range of detectors 332 equidistantly spaced along the second surface 301c as shown in FIG. 3b. The detectors are identified numerically from 1 to 7. In one embodiment, the quantity of detectors used determines the detection resolution. Because of the equidistant positions of the detectors, the intensity level measured by an individual detector corresponds to a certain height position in the Y-direction over the exposed surface 301a as indicated on FIG. 3b. The detector types can be a ROSA (Receiver optical sub-assembly), an optical fiber, or other.

Referring back to FIG. 1, the sensor 100 is shown after a certain amount of material 150 accumulation, which in this embodiment is ice. The scenario shows partial ice coverage of the monitored surface 180 and of the exposed surface 101a. The first portion 130a of the beam 130 that is incident upon the exposed surface 101a above the ice bordering the air-medium experiences TIR and be reflected onto detectors 5, 6 and 7. The second portion 103b of the beam 130 encounters ice at the exposed surface 101a. Because ice has a refractive index of n=1.31, which is less than limiting refractive index value of n>1.42 providing TIR, a substantial amount of the second portion of the beam will be transmitted into the ice as shown. See table A below for two examples of inclined material/medium interfaces.

TABLE A

| Combination ID | interface @ 850 nm from/to | Interface Inclination φ (degrees) | Refr Index Ultem n | Refr Index BK7 Glass n | Refr Index Air n | Refr Index Ice n | Reflected Power % | Transmitted Power % | Refracted beam angle θ (degrees) |
|---|---|---|---|---|---|---|---|---|---|
| A1 | Ultem/Air | 45 | 1.64 | NA | 1.00 | NA | 100 | 0 | TIR |
| A2 | Ultem/Ice | 45 | 1.64 | NA | NA | 1.31 | 5.3 | 94.7 | 62.3 |
| B1 | Glass/Air | 45 | NA | 1.51 | 1.00 | NA | 100 | 0 | TIR |
| B2 | Glass/Ice | 45 | NA | 1.51 | NA | 1.31 | 1.5 | 98.5 | 54.6 |

(material attenuation is negligible)

The combinations of A1 and B1 experience TIR as previously discussed. This means that all the power is reflected toward the detectors, yielding maximum power detection. For combination A2, 94.7% of the power is transmitted into the ice mass with a refraction angle of θ=62.3° relative to the interface normal. This energy will dissipate into the ice. A small fraction of 5.3% is reflected toward the detectors, yielding little power detection. Combination B2 will perform similar to A2, but with slightly different numbers as shown.

The controller functions to calculate the level of material accumulation. The controller can be any known processor unit comprising a digital processor and associated memory. The controller can be integrated with the sensor or it can be discrete from the sensor. Likewise, the sensor can be provided with the controller, or the components can be provided separately. As a discrete component, the controller can be a standalone computer, including a computer integrated into an aircraft's control panel, or a personal computer such as a laptop, tablet or smartphone. Furthermore, as a discrete component, one controller can support one or more sensors. In one embodiment, one controller is connected to two or more sensors. The controller can be configured to receive optical or electrical signals. For example, in one embodiment, the reflected light is converted in the sensor and transmitted to the controller as an electrical signal. In another embodiment, the reflected light is transmitted to the controller as an optical signal and the controller converts it to an electrical signal. In still another embodiment, the controller has an optical processor (or an optical programmable integrated circuit (PIC)), thereby obviating the need to convert the optical signals to electrical signals. Still other embodiments will be obvious to one of skill in the art in light of this disclosure.

The controller can function is various ways. For example, in one embodiment (method 1), the controller calibrates the output with air as the medium and creates a TIR calibration factor equal to the sum of all TIR detector outputs with the contribution from each detector ideally being the same when the medium is air. When ice accretes during flight, the combined detector output is then compared to the TIR calibration factor and the ice thickness can be scaled based on the fraction of the combined detector response versus the calibrated TIR factor. Using FIG. 1 as an example, this means that the contributions from detectors 1+2+3+4 can be ignored due to the 95-98% transmission into the ice with little reflection reaching the detectors, and only the TIR to detectors 5+6+7 will form the fraction relative to the TIR calibration factor.

In another embodiment (method 2), the controller calculates the level of accumulation using an electronic threshold applied to each detector. Thus, when a specific detector shows a response below a preset threshold, it will be ignored and indicate that the ice level is between the height corresponding to this detector and the next detector which has an output above its preset threshold. As an example, if the ice accumulation is at a level as shown in FIG. 1, detectors 1, 2, 3 and 4 will all have outputs below the threshold (and be ignored) while the outputs from detectors 5, 6, and 7 will be above the threshold. It can then be determined that the ice accretion is at a height between Y4 and Y5. A display could show a bar of light proportional and calibrated to a height scale or it could turn on LED's indicating the height of ice on a calibrated dimensional scale. Audible warnings can also be applied. However, for unmanned aircraft (UAV), electronic feedback activation of heating coils or other means to melt the accretion may be implemented. Successful application of the second embodiment (method 2) requires typically, although not necessarily, that the intensity level across the entire beam profile is the same (discussed below). While the first embodiment-(method 1) might be less sensitive to the intensity profile, a uniform intensity distribution is also preferred here.

Figure 2:
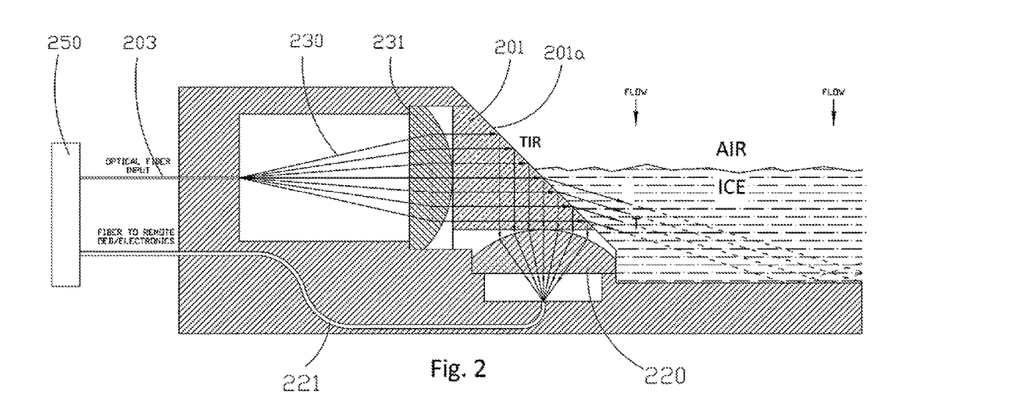
FIG. 2 shows another embodiment of the invention similar to that of FIG. 1, but with an aggregating lens on the light receiver.

The embodiment of FIG. 2 provides yet another option (method 3), using one optical source and one optical detector, where the reflected light is aggregated via a lens back to the single detector and the measured output is then related fractionally to a pre-determined calibration factor obtained by using the same single detector to collect the TIR light from all sources when the fluid is air with no material accumulation present.

Figure 9:
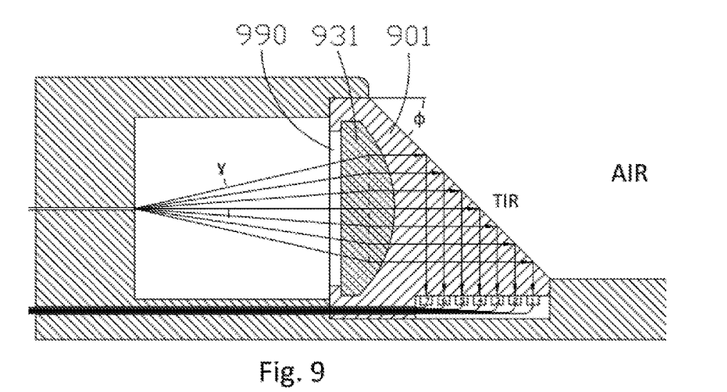
FIG. 9 shows another embodiment of the sensor of the present invention with a lens disposed in a cavity of the optically-transparent body.

Embodiments for launching or delivering light along the length of the exposed surface can vary. For example, in one embodiment, shown in FIG. 2, a single fiber 203 (as shown in FIG. 2) emits light into a lens 231, which spreads and collimates the beam 230 along the length of the exposed surface 201a. The configuration of the lens has a variety of different embodiments. In FIGS. 1 and 2 the lens is a discrete lens, outside of the body 101, 201. This results in a very simple body 101, 201, which can be, for example, a simple prism. Other lens configurations are possible. For example, in the embodiment of FIG. 9 the lens 931 may be disposed in a defined cavity 990 defined with the body 901. In yet another embodiment, the lens may be integrally molded with the body (not show). Typically, use of discrete components (e.g., embodiment of FIGS. 1-3) is more economical for small quantities, whereas for larger quantities, the use of integrated components (e.g., embodiment of FIG. 9) may be preferred. Still other embodiment will be oblivious to those of skill in the art in light of this disclosure.

Figure 5:
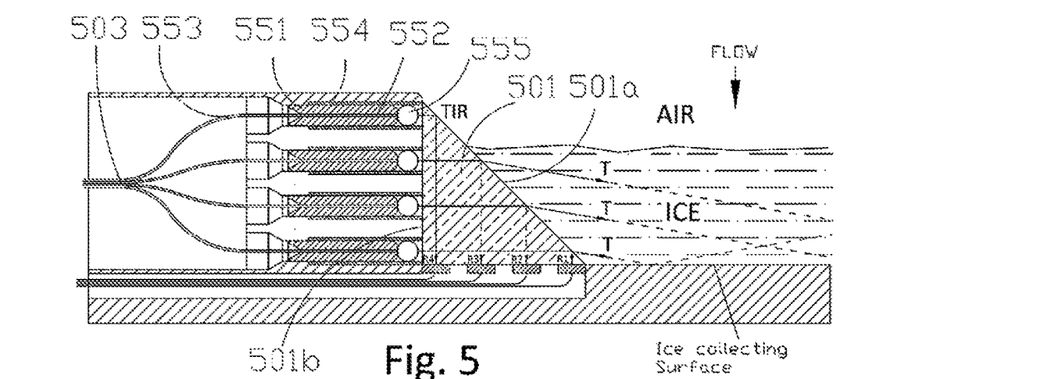
FIG. 5 shows yet another environment of the present invention showing individual fibers and lenses for the light delivery source.

In the embodiments of FIGS. 1 and 2, the delivery source is a single fiber. It should be understood, however, that other embodiments are possible. For example, in FIG. 5, a multiple fiber light delivery source 503 is shown. Specifically, in this embodiment, each fiber 553 is terminated in a ferule assembly 551 comprising a sleeve 554 containing a ferrule 552 and a ball lens 555 contacting the fiber 553. Each ferrule assembly 551 is position to deliver a collimated beam at a certain point along the length of the exposed surface 501a. The body 501 is a simple prism, which has a straight first surface 501b. This provides a design which is well disposed for repair and maintenance since the launch fibers and lenses can be removed and re-installed individually In yet another embodiment, a multiple fiber delivery source 603 is disclosed in the sensor 600 of FIGS. 6a-6e. This embodiment does not require a lens(es). Specifically, in this embodiment, each fiber 653 is disposed proximate to a particular facet 660 of the exposed surface 601a. The fiber end is close enough to the facet such that no lens, or collimation of the beam, is necessary (see, FIG. 6d). This embodiment is discussed in greater detail below.

As mentioned above, the light delivery source distributes the light along the length of the exposed surface. In one embodiment, the light is distributed evenly or substantially evenly. A more reliable correlation to reflected light and accumulation on the exposed surface will be achieved if the light is evenly distributed. In other words, the calibration will be more accurate if more light is available to be reflected/transmitted. The more light that is available for transmission/refection the greater the sample size and the more accurate the measurement.

Figure 4:
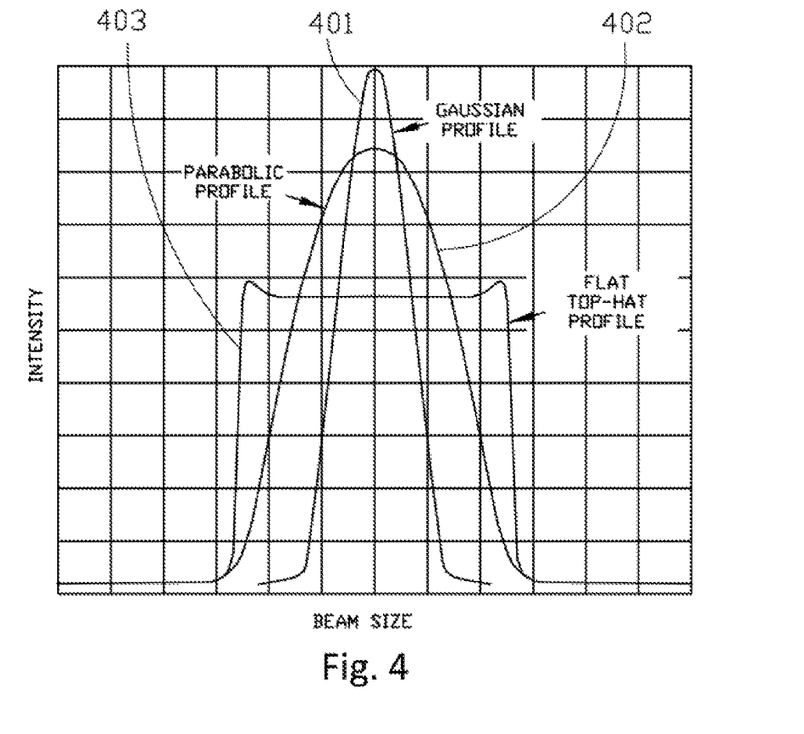
FIG. 4 shows varying intensity profiles of light incident on the exposed surface.

For example, referring to FIG. 4, different intensity profiles along the length of the exposed surface are considered. FIG. 4 depicts three different intensity distributions typically encountered from optical fibers. The Gaussian intensity profile 401 is similar to the output from a single mode fiber where most of the power is concentrated in the central part of the beam and therefore is not suited for the application. The parabolic profile 402 is similar to the output from a typical multimode graded index fiber where the power is distributed over a larger central beam area but falls off with increased beam radius. The preferred intensity distribution for the invention is the so-called top-hat profile 403, which approximates equal intensity across the entire beam size. This is achievable with use of a step-index large core fiber and a launch condition providing a fully filled fiber. This core size can be 200 microns or larger. Other means of beam shaping for providing a top-hat intensity distribution are also possible. In one embodiment, the light delivery source is configured for delivering light to the body such that the light varies along the length by less than 50% of maximum intensity across the intensity profile, and in a particular embodiment, by less than 15% of maximum intensity across the intensity profile.

Still other embodiments of the light delivery source will be known to those of skill in the art in light of this disclosure.

The light receiver functions to collect the light reflected from the exposed surface. To this end, in a simple embodiment, the light receiver comprises a lens 220, which focuses the light into a fiber 221 as shown in FIG. 2. In this embodiment, there is no resolution with respect to the intensity of the reflected light corresponding to different points along the exposed surface 201a. Rather the light along the second surface 201c is aggregated for processing.

In this particular embodiment, the light from the lens 220 is coupled to a fiber 221 where the light is then transmitted to a discrete opto-electrical device (OED) (not shown) where the light is converted to an electrical signal for analysis in the controller as discussed above. Alternatively, rather than the lens coupling with the fiber, the lens may couple directly with the OED, and an electrical signal is transmitted to controller.

In another embodiment, the light receiver functions not only to collect the reflected light, but also to provide resolution as to the lights point of collection along the second surface of the body. To this end, in one embodiment, a plurality of receivers 103 are disposed along the second surface 103c as shown in FIG. 1. As described above, by using a plurality of receivers, the intensity of the reflected light can be measured at specific points along the second face which, because the reflected beam is predictable, correspond to the certain points along the length of the exposed surface.

Figure 10:
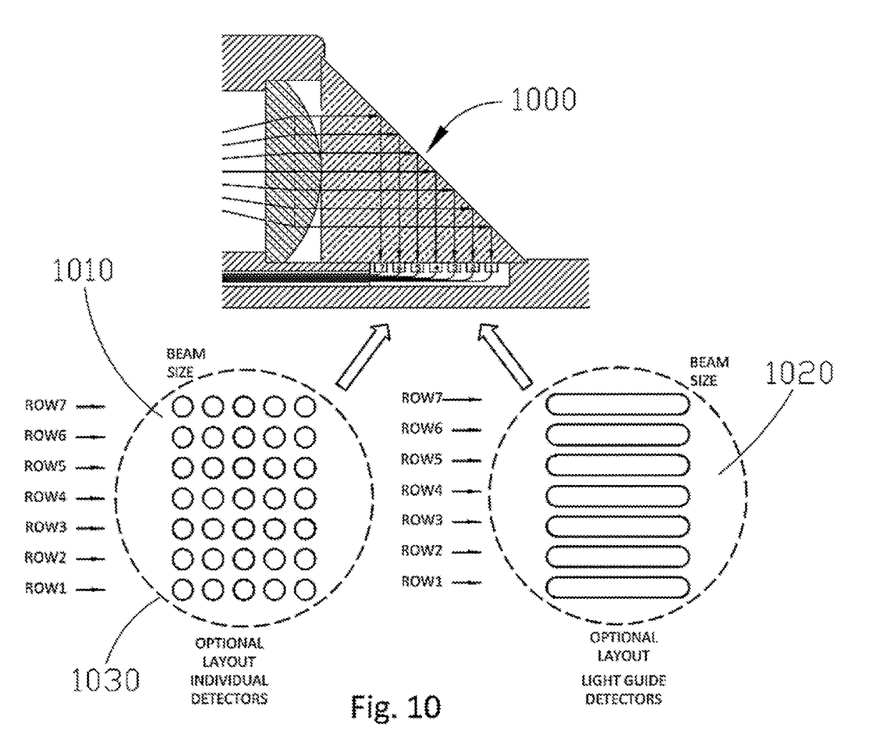
FIG. 10 shows an embodiment of the sensor having a two-dimensional array of receivers.

In another embodiment, to increase the level of light collection, a two dimensional array of receivers 1010 can be used in sensor 1000 as shown in FIG. 10. In the embodiment of FIG. 10, the array of receivers 1010 can be positioned in circular pattern covering the diameter of the reflected beam spot 1030, or as an array of light guide detectors 1020 extending parallel to the monitored surface. The output from each row in the array or extended light guide will still correspond to a designated scaled material height.

This increased resolution provides for additional analytics. For example, if the ability to distinguish between different ice types (e.g., snow, rime ice and solid ice or a mixture) is desired, more sophisticated electronics shall be applied. Rime ice is opaque and less dense than the solid ice. The white opaque appearance is caused by bubbles trapped in the ice and Mie-scattering therefore reduces the optical transmittance through rime ice or mixtures. As a result, when rime ice is present, scattering will return some of the light to the detectors. The amount of light returned is between that of the air and of ice, although closer to air. It is thus necessary to include intermediate thresholds to the signal processing, and, in one embodiment, a more precise calibration of the detection system. Because of the individual outputs from the discrete detectors of measuring method 1 and their individual height calibrations, the system is able to identify both the layered combinations of the different ice forms and their thicknesses.

The body functions to receive light, transmit the light to its exposed surface, and transmit reflected light from the exposed surface to the light receiver. The body and exposed surface can vary in configuration. As mentioned above, in FIGS. 1-3a, the body is a simple prism with a singular planar exposed surface.

Figure 6A:
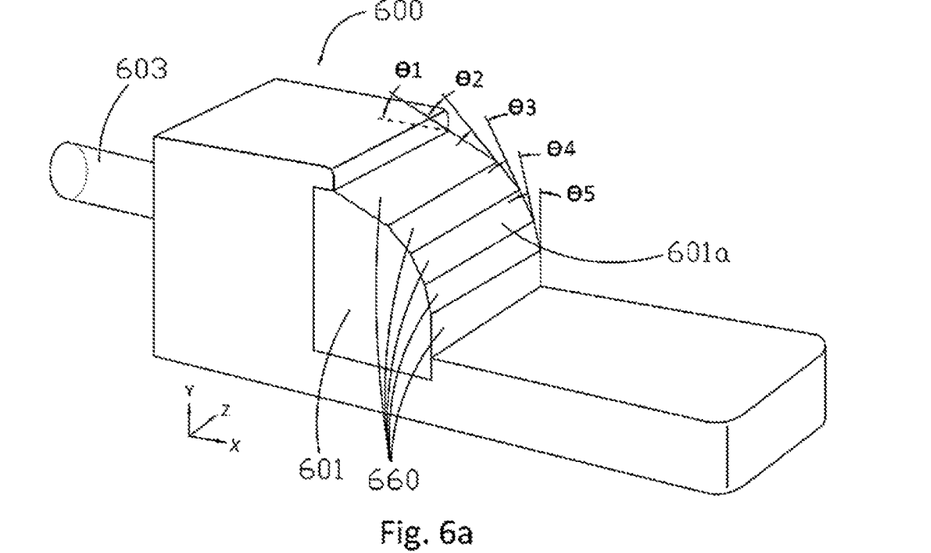
FIGS. 6a-6e show yet another environment of the invention showing a plurality of facets on the lens body.
Figure 6B:
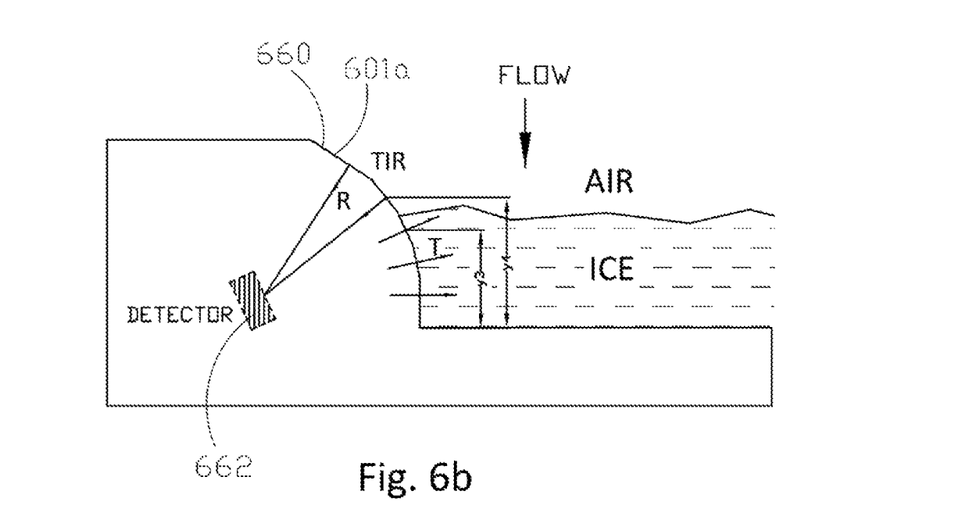
Figure 6C:
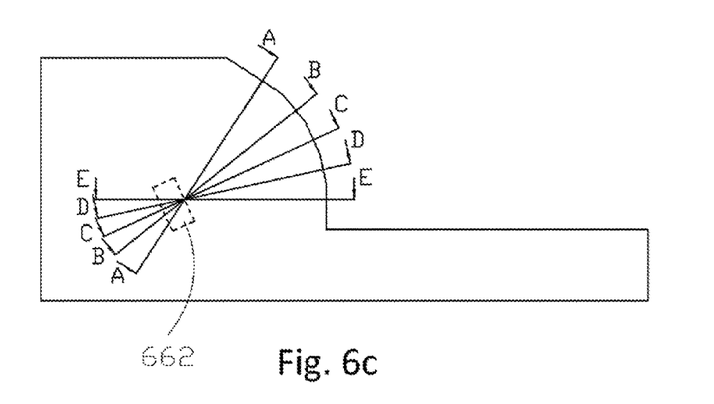
Figure 6D:
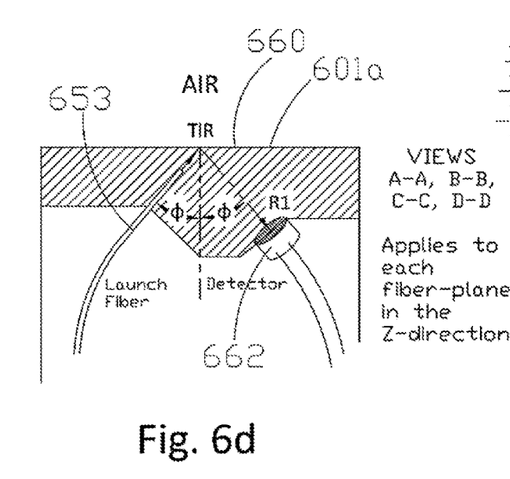
Figure 6E:
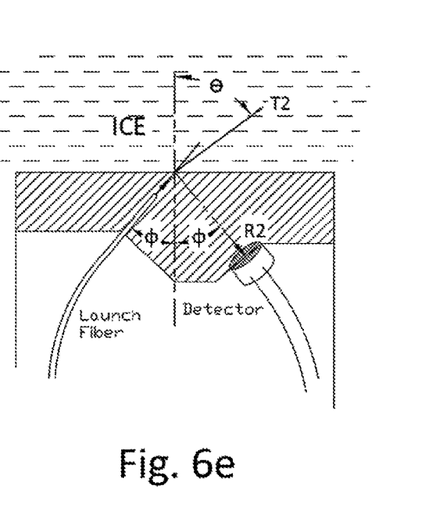

Alternatively, a multifaceted exposed surface may be used, as shown, for example, in FIG. 6a-e. As mentioned above, in this embodiment, the launch fibers are individual and no lenses are used. The different facets 660 of the exposed surface 601a of the optically-transparent body 601 are inclined with an angle θ(x), which is matched to each individual fiber in such a manner that when air is the medium being investigated the second surface will provide TIR for the beam directing it towards one single shared detector. Together the facets form a curve defining a convergence point. Each facet provides TIR for the beam directing it towards one single shared detector 662 at the convergence point. The centers of the individual exposed surfaces are equidistant from the reference surface as shown in FIG. 6c. FIGS. 6d-e show cross-sectional views of each plane A-A, B-B, C-C, D-D and E-E. The optical concept used is the same as described previously and the examples of table A will also apply for this design. The exception is that all the reflected light goes to one common shared detector instead of to individual detectors. Determination of the material thickness is accomplished, in one embodiment, by comparing the accumulated detected intensity to that of the total intensity measured and calibrated when the medium is air. The calibration factor then determines the thickness.

Figure 7:
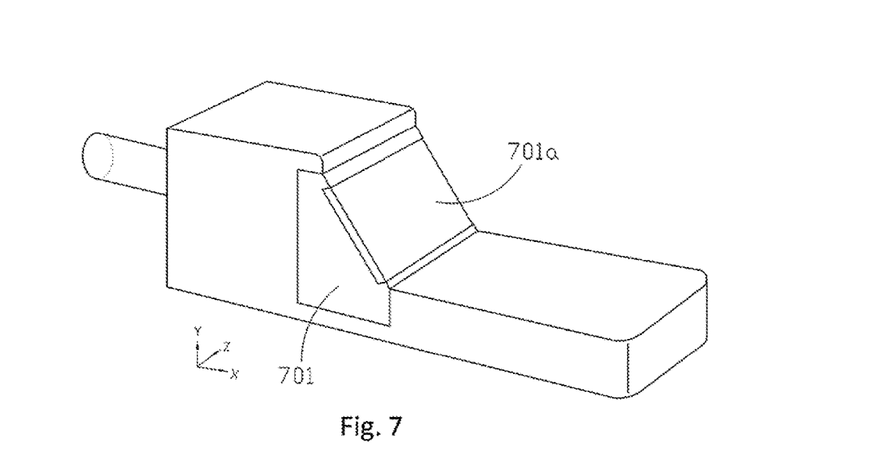
FIG. 7 shows an embodiment of the present invention having a removable exposed surface.

Referring to FIG. 7, in one embodiment, the exposed surface 701a is discrete from the body 701. Such an embodiment facilitates replacement and repair of the only element of the sensor in contact with the environment. Specifically, during regular use and maintenance, it is possible that the optical surface can get damaged or scratched. If the transmitting medium is manufactured from a molded polymeric material, it may be advantageous to use a protective and replaceable window. FIG. 7 shows an example where a window is applied to the design of FIG. 2. The window may also be applied to the embodiment of FIG. 6. The optical effect of mounting a window will only be minor, especially if the window material is the same as the body. If it is a combination of materials with close refractive indices, Ultem and Glass for example, the inclined interface angle Φ between the optically-transparent body and the window shall be adjusted to assure that the incoming beam onto the window/medium interface provides TIR. This will also cause the reflected power to return to the detectors with a slightly different angle than without the use of a window. All that is required to compensate from this is a small shift of the detector positions.

The sensor should be configured such that the length of the exposed surface runs along the axis of accumulation of the material. In other words, it is anticipated that the material will accumulate in a certain direction, e.g. vertically, and the exposed surface should be disposed such that the exposed surface extends in that direction, e.g. vertically. Therefore, when referring to the exposed surface extending along the axis of accumulation, this means that movement along the axis of accumulation results in movement along length l. It should be understood that although the length of the exposed surface needs to extend along the axis of accumulation, it need not be parallel or coincident with that axis. For example, in the embodiment of FIG. 1, the exposed surface extends at a 45 degree angle with respect to the axis of accumulation. It should be appreciated that having the exposed surface angled with respect to the axis of accumulation increases the sensitivity of the sensor as the amount accumulation of material along the axis of accumulation is "stretched" along the length of the exposed surface, thereby providing for increased resolution. For example, if the exposed surface is at a 45 degree angle with the axis of accumulation, then 10 mm of accumulation will amount to 14 mm of accumulation along the length of the exposed surface, thereby increasing resolution. Thus, the exposed surface is placed in the environment such that, as the accumulation of the material increases, the material's contact along the length of the exposed surface increases.

In an application in which the sensor is used to measure accumulation of the material on a monitored surface, such as a wing component (e.g., foil), one end of the length of the exposed surface should be deposed proximate the monitored surface. That way, the material begins to contact the exposed surface as soon as it begins to accumulate on the monitored surface. Generally, the axis of accumulation will be perpendicular to the monitored surface. For example, with respect to an icing sensor, the sensor head has a flat protruding extension positioned parallel to the beam axis for ice collection. This surface must be positioned so it faces the oncoming air-flow in order to receive the same ice accretion as the surrounding parts of the aircraft. Although wing components are considered in this example, it should be understood that the sensor can be used in any application in which icing is an issue, including, for example, other components of an airplane, stabilizer, or the blades of a wind turbine or helicopter.

In another embodiment, the sensor is configured for measuring the level of scale in pipes or a vessel, wherein the material is scale and the fluid is liquid, and the monitored surface is the wall of the vessel.

In some embodiments, the sensor is used to measure the level of accumulation of a material without respect to a monitored surface. For example, in one embodiment, the sensor is used to determine the level of liquid in a tank. In this case, the direction of accumulation will be vertical (due to gravity), and the sensor is disposed at a point in which the detection of the level is critical. In this way, the sensor can be used as a limit switch—e.g., a preventive overfill off-switch in a tank being filled with an explosive fluid.

One advantage of using fibers as both emitters and detectors is that because fibers are a dielectric they do not carry electrical current, radiate energy, or produce heat or sparks. Therefore they are well suited for applications in dangerous and explosive environments.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A sensor for detecting the level of accumulation of a material along an axis in a fluid environment, said material having a first refractive index and said fluid having a second refractive index different from said first refractive index, said sensor comprising:
    a single optically transparent body having a third refractive index and at least one exposed surface defining a length, said exposed surface being configured to be exposed to said environment and positioned with said length extending at least partially in the direction of said axis, said at least one exposed surface being configured to reflect light from at least one light delivery source to at least one light receiver in a single reflection;
    said at least one light delivery source for delivering transmitted light to said body such that said transmitted light is distributed along said length of said exposed surface;
    said at least one light receiver for receiving reflected light from said length of said exposed surface, wherein the amount of said reflected light depends on the level of said material accumulated along said length of said exposed surface; and
    wherein at least one of said transmitted light or said reflected light propagates at least partially in the direction of said axis.

2. The sensor of claim 1, wherein said sensor is configured for measuring the level of accumulation of said material on a monitored surface, wherein said axis is perpendicular to said monitored surface.

3. The sensor of claim 2, wherein said sensor is configured for measuring the level of ice accumulation, wherein said material is ice and said fluid is air, and said monitored surface is the edge of a wing component.

4. The sensor of claim 2, wherein said sensor is configured for measuring the level of scale on a vessel, wherein said material is scale and said fluid is liquid, and said monitored surface is the wall of said vessel.

5. The sensor of claim 1, wherein said at least one light receiver comprises a two-dimensional array of receivers.

6. The sensor of claim 1, wherein said sensor is configured for measuring the level of a liquid in a container, wherein said material is said liquid, and said axis is vertical.

7. The sensor of claim 6, wherein said environment is flammable or explosive.

8. The sensor of claim 1, wherein said at least one exposed surface extends at an angle with said axis of accumulation.

9. The sensor of claim 1, wherein said at least one exposed surface is a single planar surface.

10. The sensor of claim 9, wherein said at least one exposed surface extends at a 45 degree angle with said axis of accumulation.

11. The sensor of claim 9, wherein said at least one light delivery source comprises a single optical fiber optically coupled to a lens.

12. The sensor of claim 9, wherein said at least one light delivery source comprises a plurality of optical fibers, each optically coupled to a lens.

13. The sensor of claim 1, wherein said at least one light receiver comprises a plurality of opto-electric devices (OEDs), each configured for receiving light reflected from a certain portion along said length of said exposed surface, and converting said received light to an electrical signal, said at least one light receiver also comprises electrical conduit for transmitting said electrical signal of each OED to a controller.

14. The sensor of claim 1, wherein said at least one light receiver comprises a lens for focusing said light reflected from said exposed surface to at least one OED for converting the focused light to an electrical signal, and an electrical conduit for transmitting said electrical signal of said OED to a controller.

15. The sensor of claim 1, wherein said at least one exposed surface comprises a plurality of planar facets forming a curved exposed surface and defining a convergent point of light reflected by said facets.

16. The sensor of claim 15, wherein said at least one light delivery source comprises an optical fiber optically coupled to each facet.

17. The sensor of claim 14, wherein said at least one light receiver comprises a single OED disposed proximate said convergent point and an electrical conduit from said OED to said controller.

18. The sensor of claim 1, wherein said at least one light receiver comprises a light conduit for transmitting said reflected light to a discrete OED.

19. The sensor of claim 1, wherein said exposed surface is discrete from said body.

20. The sensor of claim 19, wherein said exposed surface is replaceable.

21. The sensor of claim 1, further comprising:
a controller to determine said level of accumulation of said material along said length of said exposed surface based on at least said reflected light.

22. The sensor of claim 21, wherein said reflected light comprises at least a first portion of said light reflected at said exposed surface as a function of said first and third refractive indexes, and a second portion of said light reflected at said exposed surface as a function of said second and third refractive indexes, and wherein said controller determines the level of accumulation of said material on said exposed surface based on the relative amounts of said first and second portions in said reflected light.

23. The sensor of claim 1, wherein said at least one light delivery source is configured for delivering light to said body wherein the intensity of incident light on said exposed surface varies by less than 15% of the maximum intensity across the intensity profile.

24. The sensor of claim 1, wherein at least one of said transmitted light or said reflected light is essentially parallel to said axis.

25. A method for detecting the level of accumulation of a material along an axis in a fluid environment, said material having a first refractive index and said fluid having a second refractive index different from said first refractive index, said method comprising:
transmitting at least one incident beam along a length of at least one exposed surface of a single optically transparent body having a third refractive index, said at least one exposed surface being configured to be exposed to said environment and positioned with said length extending at least partially in the direction of said axis, said at least one exposed surface being configured to reflect said incident light in a single reflection to create reflected light; and
receiving said reflected light from said length of said exposed surface, wherein the amount of said reflected light depends on the level of said material accumulated along said length of said exposed surface; and
wherein at least one of said incident light or said reflected light propagates at least partially in the direction of said axis.

26. The method of claim 25, wherein at least one of said incident light or said reflected light is essentially parallel to said axis.

27. A sensor in combination with am structure having a monitored surface, said sensor for detecting the level of accumulation of a material along an axis in a fluid environment, wherein said axis is perpendicular to said monitored surface, said material having a first refractive index and said fluid having a second refractive index different from said first refractive index, said sensor comprising:
a single optically transparent body having a third refractive index and at least one exposed surface defining a length, said exposed surface being exposed to said environment and positioned with said length at least partially along said axis, said at least one exposed surface being configured to reflect light from at least one light delivery source to at least one light receiver in a single reflection;
said at least one light delivery source for delivering transmitted light to said body such that said transmitted light is distributed along said length of said exposed surface;
said at least one light receiver for receiving reflected light from said length of said exposed surface, wherein said reflected light depends on the level of said material accumulated along said length of said exposed surface;
wherein at least one of said transmitted light or said reflected light propagates at least partially in the direction of said axis; and
a controller to determine said level of accumulation of said material along said length of said exposed surface based on at least said reflected light.

28. The sensor of claim 27, wherein at least one of said transmitted light or said reflected light is essentially parallel to said axis.

* * * * *